April 4, 1972 C. MEYER Plant Pat. 3,097
ROSE PLANT
Filed March 30, 1970
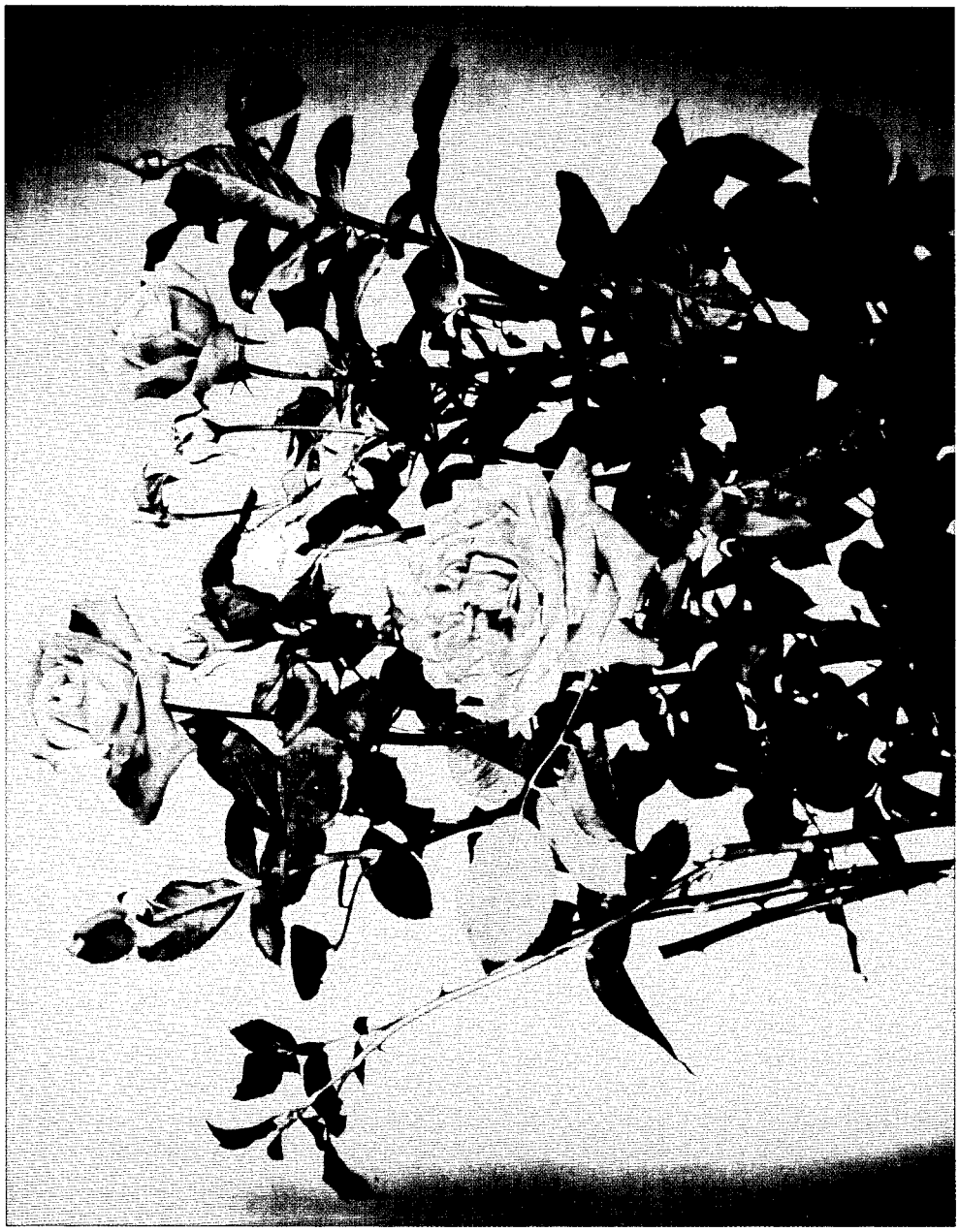
Carl Meyer
Inventor
By
Burns, Doane, Benedict, Swecker & Mathis
Attorneys

United States Patent Office

Plant Pat. 3,097

Patented Apr. 4, 1972

3,097

ROSE PLANT

Carl Meyer, Cleves, Ohio, assignor to The Conrad-Pyle Company, West Grove, Pa.

Filed Mar. 30, 1970, Ser. No. 24,041

Int. Cl. A01h *5/00*

U.S. Cl. Plt.—11 1 Claim

ABSTRACT OF THE DISCLOSURE

A rose plant of the hybrid tea class obtained by crossing a variety known as Pink Parfait (Plant Patent No. 1,904) with a variety known as Pink Peace (Plant Patent No. 1,759).

SUMMARY OF THE INVENTION

The present invention relates to a new and distinct variety of rose plant of the class known as hybrid tea, which was originated by me as a result of crossing the variety known as Pink Parfait (U.S. Plant Patent No. 1904) with the variety known as Pink Peace (U.S. Plant Patent No. 1759).

The primary objective of this crossing was to produce a new rose variety combining the most desirable characteristics of both its parents. This objective was fully achieved, along with other improvements, as shown by the following unique combination of outstanding features which differentiate my new variety from its parents and all other rose varieties of which I am aware:

(1) Exceptional vigor, very freely branched with an upright habit of growth;

(2) An unusual quantity of foliage medium large, moderately heavy and leathery and covering the branches well;

(3) Abundant and continuous flowering, greater than its seed parent and at least equal to its pollen parent, although not as large flowers as its pollen parent;

(4) An attractive bud and flower form. High centered and fully double with flowers borne one to a stem; and (5) A general flower color of medium pink shaded to lighter pink tones and deeper pink tones and diffused with pale yellow tones blended in a unique combination.

In comparison to its seed parent, the bush is more freely branched, vigorous and fully covered with leaves more glossy and of darker color; with the flowers having more petals and of more constant medium pink color that holds for the life of the bloom.

In comparison to its pollen parent, the bush is more upright in habit of growth with new shoots having more red coloring and the mature leaves more glossy; with the flowers a lighter pink with a blend of pink shades and with somewhat fewer petals.

DETAILED DESCRIPTION OF DRAWING

The accompanying drawing shows typical specimens of the flowers and foliage of my new variety in different stages of development, and as depicted in color as nearly true as it is reasonably possible to make the same in a color illustration of this character.

DETAILED DESCRIPTION OF DISCLOSURE

The following is a detailed description of my new variety with color terminology in accordance with the Color Chart of the Royal Horticultural Society, unless otherwise indicated.

Type: Hardy; tall bush outdoors; garden decoration.
Class: Hybrid tea.

Propagation: It does hold its distinguishing characteristics through succeeding propagations by cuttings, grafting, budding.

Flower

Locality where grown: West Grove, Pa.
Flowers borne: Singly, on normal, medium stems.
Quantity of bloom: Abundant outdoors.
Continuity: Continuous.
Fragrance: Moderate; tea.

Bud:

*Peduncle.*—Medium long; medium heavy; erect; light to medium green (general color term); almost smooth; few prickles; red (general color term).

*Before calyx breaks.*—Size: Medium. Form: Medium long ovoid; with foliaceous appendages on the surface of the bud; with slender little bristle-like foliaceous parts extending beyond the tip of the bud equal to ¾ or more of its length.

*As calyx breaks.*—Color: 59B (red-purple group).

*As first petal opens.*—Size: Small to medium. Form: Medium pointed. Color: Outside: 59D (red-purple group). Inside: 58B (red-purple group). Opening: It does open up well. It is retarded from opening by cold weather.

Bloom:

*Size when fully open.*—Medium, 3 inches to 3½ inches.

*Petalage.*—Very double (usually with no stamens showing) from 30 to 45 petals; arranged regularly.

*Form.*—Very full centered at first; becoming open-cupped; petals remaining at first loosely cupped or rolled outward; becoming later at maturity loosely rolled outward.

Petals: Medium soft; with inside satiny; outside satiny.

*Shape.*—Outer: Obovate; with 1 notch.

*Intermediate.*—Obovate; scalloped with apex flat; with 1 tooth.

*Inner.*—Obovate; with apex flat; with 1 notch

*Color.*—Colors may be modified by being shaded with other colors.

This description of a newly opened flower was made from a rose grown outdoors in September 1969, at West Grove, Pa.

Color: Outer petal:

*Outside surface.*—58B with some darker veining (red-purple group).

*Inside surface.*—58B, base of petal 11B near point of attachment from base upward diffused with 11A (red-purple group nad yellow group).

Intermediate petal:

*Outside surface.*—48B, base of petal 11A near point of attachment from base upward diffused with 11A (red group and yellow group).

*Inside surface.*—48B, base of petal 14A near point of attachment. From base upward diffused with 11A (red group, yellow-orange group, and yellow group).

Inner petal:

*Outside surface.*—48B, base of petal 14A near point of attachment. From base upward diffused with 11A (red group, yellow-orange group, and yellow group).

*Inside surface.*—48B, base of petal 14A near point of attachment. From base upward diffused with 11A (red group, yellow-orange group, and yellow group).

This description was made from a rose that was open for three days, outdoors in September 1969, at West Grove, Pa.

Color: Outer petal:

*Outside surface.*—58B with some darker veining (red-purple group).

*Inside surface.*—57A, lower part of petal 58B near point of attachment. Base of petal 14A (red-purple group and yellow-orange group).

Inner petal:

*Outside surface.*—62A (red-purple group).

*Inside surface.*—62B, top edge of petal 61C (red-purple group).

General color effect:

*Newly opened flower.*—62A and 62B (red-purple group).

*Three days open.*—62A, 62B and 62C with lower part of petals 62B (red-purple group).

Behavior: drop off cleanly.

*Flower longevity.*—On bush in garden 3 days in September, cut roses grown outdoors kept at living room temperature 3 days in September.

Reproductive organs

Stamens: Medium, arranged irregularly about pistils tucked in receptacle.

Filaments: Many; most with anthers; medium. Color: 32A (orange-red group).

Anthers: All open at once; medium. Color: 34A aging to 46A (orange-red group and red group). Seldom an anther fused with a petaloid.

Pollen: Sparse; gold (general color term).

Pistils: Medium.

Styles: Uneven; short; thin; bunched columnar.

Stigma: Yellow (general color term).

Ovaries: All enclosed in receptacle.

Hips: Short, flat, globular, with inconspicuous neck; smooth; walls thick dry; green (general color term).

Sepals: Permanent; medium; recurved.

Seeds: Medium quantity, medium size.

Plant

Foliage:

*Leaves.*—Compound of 3 and 5 leaflets; abundant; medium large; moderately heavy, leathery.

*Leaflets.*—Shape: Ovoid with apex acute, base obtuse, simply serrate.

*Color.*—Mature—upper surface: 139B (green group). Under surface: 137C (green group). Young—Upper surface: 178A (greyed-red group). Under surface: 178A (greyed-red group).

*Rachis (the supporting stem of the compound leaf).*—Medium. Upper side: Grooved, prickly. Under side: Moderately thorny.

*Stipules.*—Medium long; narrow; with medium points; turning out at an angle of less than 90°.

*Disease.*—Resistance comparable or superior to the average variety growing under the same cultural conditions.

Growth:

*Habit.*—Bushy, upright, much branched.

*Growth.*—Vigorous.

*Canes.*—Medium heavy.

*Main stems.*—Dull. Color: 138A (Green group).

*Prickles.*—Few. Color: 178B (greyed-red group).

*Hairs.*—None.

*Branches.*—Dull. Color: 138A (green group).

*Prickles.*—Few. Color: 178B (greyed-red group).

*Hairs.*—None.

*New shoots.*—Dull. Color: 138A (green group).

*Prickles.*—Few. Color: 178A (greyed-red group).

*Hairs.*—None.

I claim:

1. A new and distinct variety of rose plant of the hybrid tea class, substantially as herein shown and described, characterized particularly as to novelty by its unique combination of exceptional vigor, unusually freely branched and with an upright habit of growth; excellent, glossy, dark green foliage that covers the branches very well and having better than average diseases resistance when compared to other varieties of its class; unique coloration of the bloom of medium pink, being shaded with both darker and lighter pink tones and diffused with pale yellow, and unusual floriferousness with the flowers coming continuously of good size and nearly always one to the stem, fully double, seldom showing stamens in the open bloom and with color holding well until the petals fall cleanly, with moderate tea fragrance.

No references cited.

ROBERT E. BAGWILL, Primary Examiner